United States Patent
Westgarth

(10) Patent No.: US 10,441,468 B2
(45) Date of Patent: Oct. 15, 2019

(54) SPORT GOGGLE STRAP

(71) Applicant: John Westgarth, San Marcos, CA (US)

(72) Inventor: John Westgarth, San Marcos, CA (US)

( * ) Notice: Subject to any disclaimer, the term of this patent is extended or adjusted under 35 U.S.C. 154(b) by 437 days.

(21) Appl. No.: 14/830,176

(22) Filed: Aug. 19, 2015

(65) Prior Publication Data

US 2016/0067097 A1    Mar. 10, 2016

Related U.S. Application Data

(60) Provisional application No. 62/048,075, filed on Sep. 9, 2014.

(51) Int. Cl.
*A61F 9/02* (2006.01)
*A63B 33/00* (2006.01)

(52) U.S. Cl.
CPC ............... *A61F 9/027* (2013.01); *A61F 9/02* (2013.01); *A63B 33/002* (2013.01)

(58) Field of Classification Search
CPC .......... A61F 9/02; A61F 9/027; A63B 33/002
See application file for complete search history.

(56) References Cited

U.S. PATENT DOCUMENTS

| | | | | |
|---|---|---|---|---|
| 5,046,200 A * | 9/1991 | Feder | ..................... | A61F 9/027 128/207.11 |
| 5,408,702 A * | 4/1995 | Chiang | ................ | A63B 33/002 2/428 |
| 5,813,056 A * | 9/1998 | Ambrose | ............. | A63B 33/002 2/428 |
| 6,138,287 A * | 10/2000 | Chou | ................... | A63B 33/002 128/207.11 |
| 2003/0172445 A1* | 9/2003 | Kawashima | ............ | B63C 11/12 2/452 |
| 2005/0120468 A1* | 6/2005 | Kawashima | ............ | A61F 9/026 2/444 |
| 2005/0241051 A1* | 11/2005 | Matsumoto | .......... | A63B 33/002 2/426 |
| 2012/0160989 A1* | 6/2012 | Yasuhara | ............. | A63B 33/002 248/693 |
| 2012/0233825 A1* | 9/2012 | Chou | ................... | A63B 33/002 24/68 E |
| 2013/0019386 A1* | 1/2013 | Hahn | ................... | A63B 33/002 2/431 |
| 2013/0074249 A1* | 3/2013 | Chou | ................... | A63B 33/002 2/448 |
| 2013/0139305 A1* | 6/2013 | Rao | ........................ | A61F 9/027 2/452 |
| 2013/0293826 A1* | 11/2013 | Batey | ..................... | G02C 5/001 351/62 |
| 2015/0128385 A1* | 5/2015 | Kuo | ..................... | A44B 11/006 24/193 |

(Continued)

*Primary Examiner* — Megan E Lynch
(74) *Attorney, Agent, or Firm* — Florek & Endres PLLC

(57) ABSTRACT

A sport goggle strap for affixing sport goggles to the face of a user with first and second end portions, each having a connection member for attaching the first and second end portions to opposite sides of sports goggles, and an intermediate portion between the first and second end portions having an elongated opening disposed substantially in line between the first and second end portions. The first end portion, second end portions and the intermediate portion are comprised of a unitary piece of an elastomeric material, and preferably neoprene.

20 Claims, 3 Drawing Sheets

(56) References Cited

U.S. PATENT DOCUMENTS

2015/0306460 A1* 10/2015 Donovan .............. A63B 33/002
                                                          2/442
2016/0107035 A1*  4/2016 Chou ................... A63B 33/002
                                                          2/452

* cited by examiner

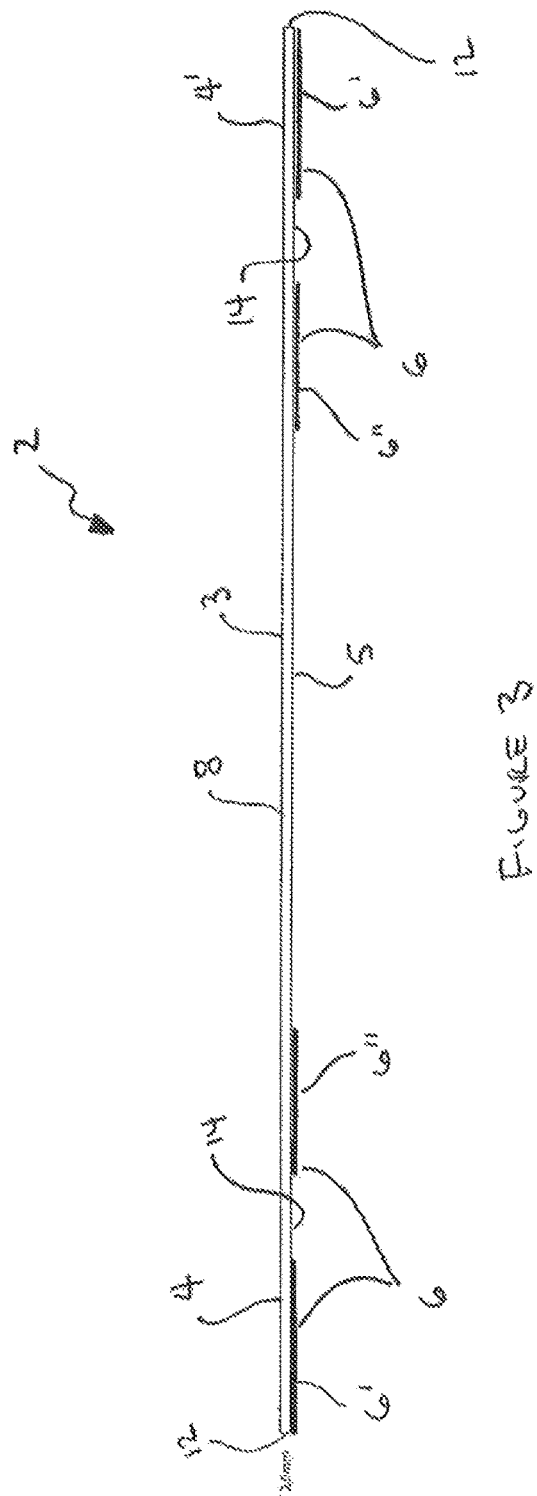

SPORT GOGGLE STRAP

FIELD OF THE INVENTION

The present invention relates to a strap for holding sport goggles, glasses and similar eyewear on the head of a user.

BACKGROUND OF THE INVENTION

Sports goggles, used herein to describe all types of sports eyewear including protective prescription and non-prescription goggles, prescription and non-prescription glasses, etc., with all types of vision correcting or enhancing lenses or without lenses to function solely as protection to the area of the eyes, are commonly used during sports and athletic activities. Such sport goggles are used by participants to not only provide clear vision, but may also be required protection for the user's eyes.

Although eye protection can be incorporated into other headgear, such as a helmet, many types of sport goggles are held on the user's head by the use of one or more straps that attach to the frames of the sport goggles. Such straps generally engage each side of the sports goggle frame and extend behind the user's head. Most often these straps are adjustable through the use of buckles on one or more sides of the strap and are often elastic to hold the sports goggles on the user's head and in proper position over the user's eyes so that the sport goggles do not move and interfere with the user during play.

Moreover, the sport goggle straps known in the art are usually one or more thin rubber bands that are attached to each side of the sport goggle frames and wrap around the back of the user's head. These straps are most problematic for girls with longer hair, where the placement of the straps often interferes with the girls' ponytails.

U.S. Pat. Nos. 6,428,167 and 7,992,228 are two patents that attempt to address the need for a sport goggle strap for use with a girl's ponytail. However, these attempts are of limited benefit. More specifically, U.S. Pat. No. 6,428,167 uses a special ponytail holder member that is threaded onto a strap member formed of rubber bands. The ponytail holder member is attached to the goggle frames through the use of one or more straps with loops and buckles.

Of course, if one strap is used to reduce the number of straps, loops and buckles in U.S. Pat. No. 6,428,167, the reference admits that the strap is subject to interference with the ponytail. Moreover, once the sport goggle strap and ponytail holder member are set up they are difficult to adjust for different ponytail placement. Additionally, the ponytail holder member is a flat nylon disc that can have a stiff edge and can slide on the user's hair.

U.S. Pat. No. 7,992,228 describes a strap that uses a specialized frame connector and a specialized diverter to attach the strap to the sport goggle frame and separate two straps so that they may be placed above and below the user's ponytail. The frame connector has cooperating components that allow the parts to swivel relative to one another to move the position of the straps higher and lower on the user's head. The diverter provides a fixed angle between the straps exiting the upper and lower exits of the diverter. However, like U.S. Pat. No. 6,428,167, the item described in U.S. Pat. No. 7,992,228 is complex with many different features.

In keeping, a sport goggle strap that can accommodate a ponytail worn in different locations on the back of a user's head without adjustment of the strap and provide simple and comfortable support for sports goggles would advance the art.

SUMMARY OF THE INVENTION

The present invention is directed to a sport goggle strap for holding sport goggles on the face of a user, the sport goggle strap comprising first and second end portions, each having a connection member for attaching the first and second end portions to opposite sides of sport goggles, and an intermediate portion between the first and second end portions, said intermediate portion comprising an elongated opening disposed substantially in line between the first and second end portions, wherein the first end portion, second end portion and intermediate portion are comprised of a unitary piece of an elastomeric material.

The connection members can be any of the same or different members at each end portion of the strap that can provide a connecting engagement between one of the first or second end portions of the strap and one side of the sport goggles. The connection members can include catches, clips, snaps, buckles, clasps, buttons, fixed or swivel connectors, etc., or combinations thereof. In this regard, it is contemplated that even a dedicated connection as shown in U.S. Pat. No. 7,992,228 may be used as the connection member between one or both of the end portions of the present invention and the sides of the sport goggles to which the strap is being attached.

The preferred embodiment comprises connection members fashioned of cooperating elements that attach to one another to create a loop at the end portion of the sport goggle strap. Suitable cooperating members for use at the first and/or second end portions of the strap for attaching to one another, to form a loop through the slot at a side of the sport goggles and maintain connection with the sports goggles, include snaps, clips, snaps, hooks, clasps, buttons, etc., with cooperating hook and loop fastener portions being most preferred.

In this most preferred embodiment, one of the hook and loop cooperating elements is placed at the inside or outside of one end portion of the strap closer to the terminal end of the end portion and the other is placed on the same inside or outside of the strap between the terminal end of the end portion and the intermediate portion, preferably with a small gap between the hook and loop cooperating elements. This allows the terminal end of the end portion to be folded over, preferably toward the interior of the strap, to engage the hook and loop elements with the gap therebetween aiding in forming a loop for engaging a slot at one side of the sports goggle frame.

The hook and loop cooperating member embodiment further permits adjustment of the length of the strap, where the terminal end of the end portion can be moved closer to the intermediate portion to make the strap shorter and farther away from the intermediate portion to make the strap longer. Of course, other cooperating members may have an elongated portion or a plurality of elements for adjustment of the length of the strap, for example, using a series of snap elements along the length of the end portion of the strap closer to the intermediate portion with a single cooperating snap element at the terminal end of the end portion of the strap.

Determining whether the cooperating members should be placed on the inside or the outside of the end portions may depend on whether the size is intended to be adjusted quickly during play, where the cooperating members would be placed on the outside of the end portions, or to be more securely fastened, so as to limit inadvertent opening, where the cooperating members would be placed on the inside of the end portions.

The width of the first and second end portions at the area of the terminal ends is preferably slightly less than the slots on each side of the sport goggles, which are generally considered standard for attachment of a strap. As will be appreciated, the closer the width of the strap at the end portions to the length of the slot on the sport goggles, the less slippage there will be of the strap end portions within the slot of the sport goggles.

The strap can be made of any suitable elastomeric material, with a foamed elastomeric material being preferred, and neoprene being most preferred. Any suitable treatment to the elastomeric material can be employed, however, it is preferred that the exterior surface of the strap be printable so that the strap can be printed with indicia. This can be done with printing directly on the neoprene or on a top layer that is adhered to the neoprene. For example, the indicia can be purely ornamental, including aesthetically pleasing prints, or at least partially functional, including team colors and names, player names or numbers, etc., screened onto the neoprene layer itself.

BRIEF DESCRIPTION OF THE DRAWINGS

The attached drawings are intended to better illustrate a preferred embodiment of the present invention without limiting the invention in any manner whatsoever.

FIG. 3 is a bottom elevation of the sports goggle strap of FIG. 1 in its fully open configuration.

DETAILED DESCRIPTION OF THE PREFERRED EMBODIMENT

The following description of the preferred embodiment is presented to describe the present invention without limiting the scope of the appended claims in any manner whatsoever.

Figure 1:
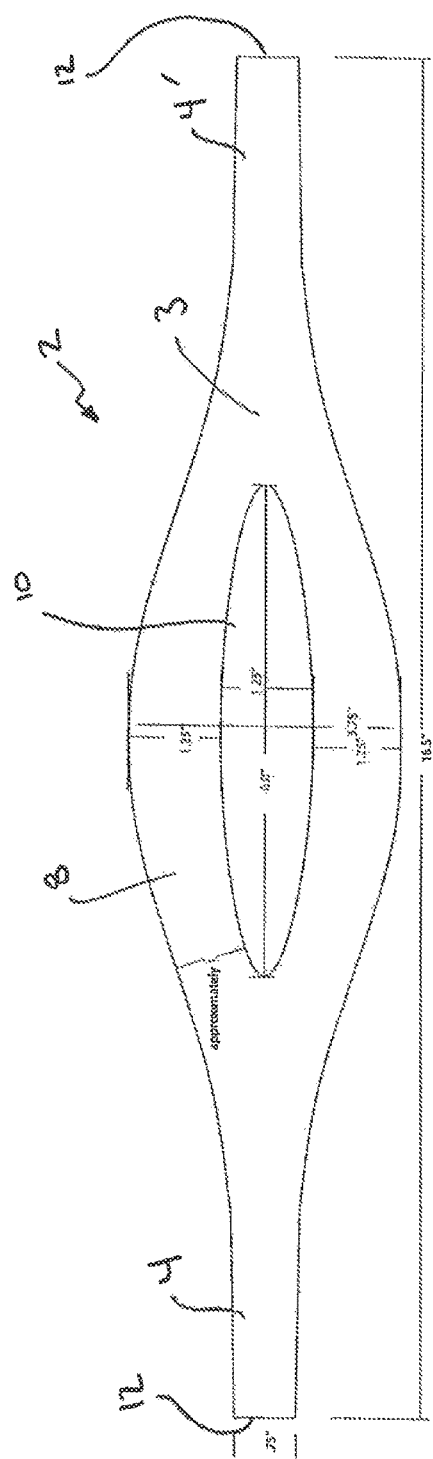
FIG. 1 is a front elevation of a sport goggle strap according to the teachings of the present invention in its fully open configuration.
Figure 2:
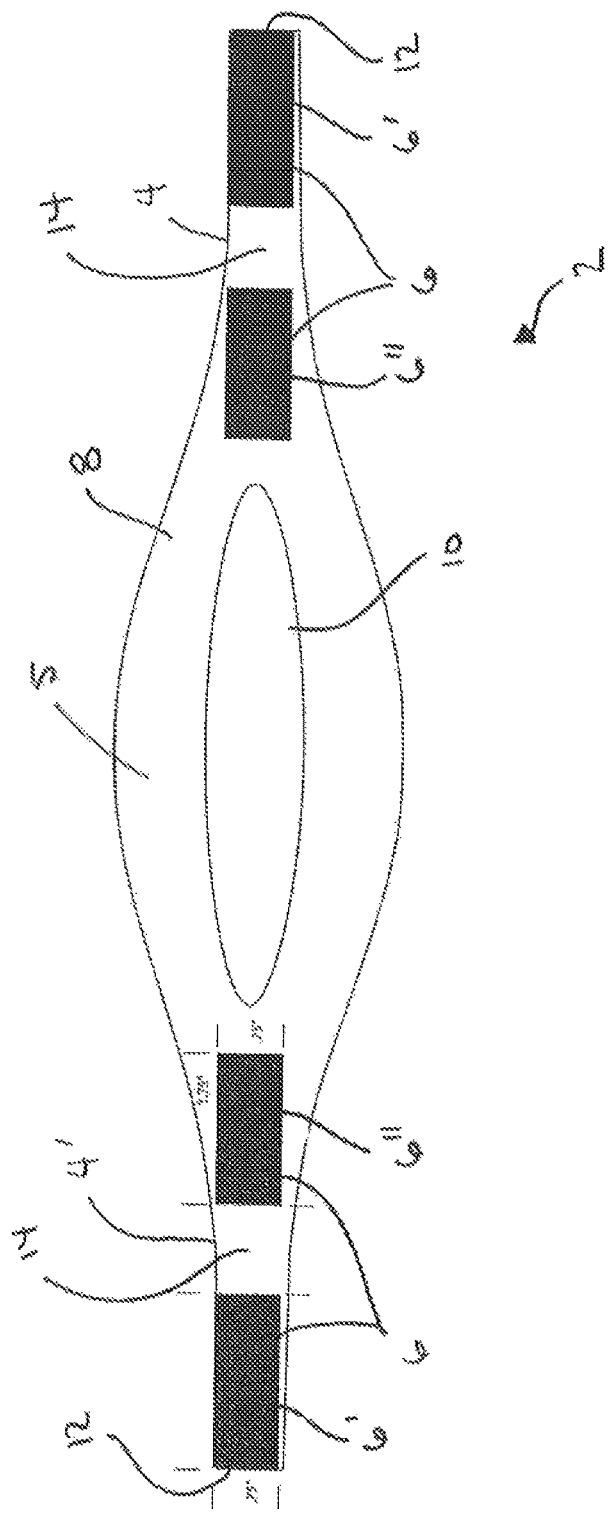
FIG. 2 is a rear elevation of the sport goggle strap of FIG. 1 in its fully open configuration.

As shown in FIGS. 1-3, the present invention is directed to a sport goggle strap 2 comprising a first end portion 4 and a second end portion 4', each of said end portions 4, 4' having a connection member 6 for attaching the first and second end portions to opposite sides of sport goggles (not shown) and an intermediate portion 8 between the first and second end portions 4, 4'. The intermediate portion 8 comprises an elongated opening 10 disposed substantially in line between the first and second ends 4, 4' with top and bottom components above and below the elongated opening, respectively.

Most preferably, the first end portion 4, second end portion 4' and intermediate portion 8 are comprised of a unitary piece of an elastomeric material. As shown in the attached drawings, and particularly FIG. 3, a foamed elastomeric material such as neoprene is most preferred, providing a soft and resilient but substantial structure to the strap 2. Any suitable treatment to the elastomeric material as known in the art can be employed, including coating one or all surfaces of the strap 2, molding indicia using a hot press roller to form indicia into a surface of the strap 2, spraying or screening indicia such as a design onto the strap 2 or adding a top layer of another material to the unitary body of the strap 2, by any means including adhesives, heat bonding, sonic welding, etc., for inclusion of the indicia on the strap 2. As described above, any indicia to be included can be purely ornamental, including aesthetically pleasing prints, or at least partially functional, including team colors and names, player names or numbers, etc.

The connection members 6 can be any of the same or different members at each end portion 4, 4' of the strap 2 so long as they can provide a connecting engagement between one of the first or second end portion 4, 4' and one side of the sports goggles, including catches, clasps, clips, snaps, buckles, clasps, buttons, fixed or swivel connectors, etc. The preferred embodiment, however, comprises cooperating elements 6' and 6" that attach to one another to create a loop at the end portion 4 of the strap 2 that engages a slot commonly included at each of the sides of the sports goggles for attachment of a strap.

Any suitable cooperating members 6 for use at the first and/or second end portions 4, 4' of the strap 2 for attaching to one another permit the terminal end of the end portions 4, 4' to pass through the slot at an end of the sport goggles and create a loop to maintain connection with the sport goggles may be used. For example, snaps, clips, snaps, buttons, hook and loop elements, etc., are possible options, with cooperating hook and loop fastener elements being most preferred.

In this most preferred embodiment, shown in FIGS. 2 and 3, one of the hook and loop cooperating elements 6' is preferably placed on one of the inside surface 5 or the outside surface 3 of the strap 2 at one end portion 4 closer to the terminal end 12 of the end portion 4 and the other of the hook and loop cooperating elements 6" is placed on the same either inside surface 5 or outside surface 3 of the strap 2 between the terminal end 12 of the end portion 4 and the intermediate portion 8. It is preferred that there is a small gap 14 between the hook and loop cooperating elements 6, 6'. This allows the terminal end 12 of the end portion 4 to be folded over in the area of the gap 14, preferably toward the interior of the strap 2, to engage the hook and loop elements 6, 6' with the gap 14 between forming a central portion of the loop for capturing one side of the sport goggle frame.

The hook and loop cooperating member design further permits adjustment of the length of the strap 2, where the terminal end 12 of the end portion 4 can be moved closer to the intermediate portion 8 to make the strap 2 shorter and, conversely, farther away from the intermediate portion 8 to make the strap 2 longer. Of course, other cooperating members 6 may have an elongated portion or a plurality of cooperating elements 6 for adjustment of the length of the strap 2. For example, use of a series of first snap elements along the length of the end portion 4 of the strap 2 closer to the intermediate portion 8, with a single cooperating second snap element at the terminal end 12 of the end portion 4 of the strap 2, will also permit adjustment to the size of the strap 2.

The dimensions of the various features of the strap 2 of the present invention are not necessarily essential to the invention, however, the preferred dimensions are shown in the drawing figures attached for use of the strap 2 with standard girls lacrosse/field hockey goggles. In this regard, the width of the first and second end portions 4, 4' at the area of the terminal ends 12 is preferably slightly less than the height of the slots on each side of the sports goggles contemplated for attachment of a strap. Additionally, the thickness of the strap 2, shown in FIG. 3 as about 2 mm, is considered preferred to permit the use of the foamed elastomeric neoprene material creating a soft and substantial engagement of the user's head.

Additionally, as shown in FIGS. 1 and 2, the elongated opening 10 has a length and a width, and the width toward the middle of the elongated opening 10 being greater than the width at the ends of the elongated opening 10. It is preferred that the width of each of the top component of the intermediate portion 8 above the elongated opening 10, the width of the middle of the elongated opening 8, and the width of the bottom component of the intermediate portion 8 below the elongated opening 10 are each between about 0.5 inches and about 2.0 inches, with about 1.25 inches being most preferred. In the most preferred embodiment, shown in FIGS. 1 and 2, the width of the elongated opening 10 at the middle of the elongated opening 10 is about the same as the width of the top and bottom components of the intermediate portion 8.

Variations, modifications and alterations to the preferred embodiment of the present invention described above will make themselves apparent to those skilled in the art. All such variations, modifications, alterations and the like are intended to fall within the spirit and scope of the present invention, limited solely by the appended claims. Additionally, all prior art referred to herein is hereby incorporated by reference.

The invention claimed is:

1. A sport goggle strap for holding sport goggles on the face of a user, the sport goggle strap comprising a unitary piece of an elastomeric material having an inside surface, an outside surface, a first end portion, a second end portion, and an intermediate portion between the first and second end portions, said intermediate portion comprising a top component above and a bottom component below an elongated opening disposed substantially in line between the first and second end portions, each of the first and second end portions comprising a connection member for attaching the first and second end portions to opposite sides of sport goggles, the connection members comprising first and second cooperating elements that attach to one another, wherein the connection members are on the same surface of the inside surface or the outside surface of the unitary piece of elastomeric material and further wherein a width of each of the top component, a middle of the elongated opening, and the bottom component are between about 0.5 inches and about 2.0 inches.

2. The sport goggle strap of claim 1 wherein the connection member on each of the first and second end portions is selected from the group consisting of hook and loop fasteners, catches, clips, snaps, buckles, clasps, buttons, fixed or swivel connectors, and combinations thereof.

3. The sport goggle strap of claim 1 wherein the first and second cooperating elements attach to one another to create a loop at at least one of the first and second end portions of the strap, wherein the loop is adapted to maintain connection of the end portion with the sport goggles.

4. The sport goggle strap of claim 1 wherein the cooperating elements are selected from the group comprising hook and loop fastener portions, snaps, clips, snaps, hooks, clasps, buttons, and combinations thereof.

5. The sport goggle strap of claim 1 wherein the first cooperating element is placed closer to a terminal end of at least one of the first and second end portions and the second cooperating element is placed between the first cooperating element and the intermediate portion.

6. The sport goggle strap of claim 1 wherein at least one of the first and second cooperating elements comprises a series of elements or an elongated portion so that the size of the strap can be adjusted.

7. The sport goggle strap of claim 5 further comprising a small gap between the first and second cooperating elements.

8. The sport goggle strap of claim 1 wherein the first and second cooperating elements are hook and loop fastener portions.

9. The sport goggle strap of claim 8 wherein the first cooperating element, being one of the hook or loop members, is placed closer to a terminal end of at least one of the first and second end portions and the second cooperating element, being the other of the hook or loop members, is placed between the first cooperating element and the intermediate portion, with a gap between the first and second cooperating elements, and further wherein at least one of the first and second cooperating elements is an elongated portion to provide a size adjustment to the sport goggle strap.

10. The sport goggle strap of claim 1 wherein the elastomeric material is a foamed elastomeric material.

11. The sport goggle strap of claim 1 wherein the elastomeric material is neoprene.

12. The sport goggle strap of claim 11 wherein the neoprene has a thickness of about 2 mm.

13. The sport goggle strap of claim 1 wherein the first and second end portions each have a terminal end with a width, the width of the terminal end being only slightly less than the height of a slot, on each side of the sport goggle, adapted to receive a strap.

14. The sport goggle strap of claim 1 wherein the elastomeric material is printed with indicia.

15. The sport goggle strap of claim 1 wherein the elastomeric material has a coating layer.

16. The sport goggle strap of claim 1 wherein the elongated opening has a length and the width at the middle of the elongated opening is greater than a width at ends of the elongated opening.

17. The sport goggle strap of claim 1 wherein the width of each of the top component, the middle of the elongated opening, and the bottom component are each about 1.25 inches.

18. The sport goggle strap of claim 1 wherein the width of each of the top component, the middle of the elongated opening, and the bottom component are substantially the same.

19. A sport goggle strap for holding sport goggles on the face of a user, the sport goggle strap comprising a unitary piece of neoprene having an inside surface, an outside surface, a first end portion, a second end portion, and an intermediate portion between the first and second end portions, said intermediate portion comprising an elongated opening disposed substantially in line between the first and second end portions, each of the first and second end portions comprising a connection member for attaching the first and second end portions to opposite sides of sport goggles, the connection members comprising first and second cooperating elements that attach to one another, wherein the connection members are on the same surface of the inside surface or the outside surface of the unitary piece of elastomeric material and the neoprene has a thickness of about 2 mm.

20. A sport goggle strap for holding sport goggles on the face of a user, the sport goggle strap comprising a unitary piece of an elastomeric material having an inside surface, an outside surface, a first end portion, a second end portion, and an intermediate portion between the first and second end portions, said intermediate portion comprising a top component above and a bottom component below an elongated opening disposed substantially in line between the first and second end portions, each of the first and second end portions comprising a connection member for attaching the first and second end portions to opposite sides of sport goggles, the connection members comprising first and second cooperating elements that attach to one another, wherein the connection members are on the same surface of the inside surface or the outside surface of the unitary piece of elastomeric material and further wherein a width of each of the top component, a middle of the elongated opening, and the bottom component are substantially the same.

* * * * *